US008200334B1

(12) United States Patent
Min et al.

(10) Patent No.: US 8,200,334 B1
(45) Date of Patent: Jun. 12, 2012

(54) SYSTEMS AND METHODS FOR REMOTE MONITORING OF SIGNALS SENSED BY AN IMPLANTABLE MEDICAL DEVICE DURING AN MRI

(75) Inventors: Xiaoyi Min, Thousand Oaks, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1102 days.

(21) Appl. No.: 11/938,088

(22) Filed: Nov. 9, 2007

(51) Int. Cl.
*A61N 1/08* (2006.01)

(52) U.S. Cl. .............................................. 607/27; 607/60

(58) Field of Classification Search ................ 607/9, 17, 607/60
See application file for complete search history.

(56) References Cited

U.S. PATENT DOCUMENTS

| | | | |
|---|---|---|---|
| 4,746,864 A | 5/1988 | Satoh | |
| 4,991,580 A | 2/1991 | Moore | |
| 5,063,348 A | 11/1991 | Kuhara et al. | |
| 5,217,010 A * | 6/1993 | Tsitlik et al. | 607/9 |
| 5,404,880 A | 4/1995 | Throne | |
| 5,800,467 A | 9/1998 | Park et al. | |
| 6,052,614 A | 4/2000 | Morris, Sr. et al. | |
| 6,675,036 B2 | 1/2004 | Kreger et al. | |
| 6,795,730 B2 | 9/2004 | Connelly et al. | |
| 7,039,455 B1 | 5/2006 | Brosovich et al. | |
| 7,164,950 B2 * | 1/2007 | Kroll et al. | 607/36 |
| 7,729,770 B2 * | 6/2010 | Cabelka et al. | 607/37 |
| 2003/0083570 A1 | 5/2003 | Cho et al. | |
| 2003/0144704 A1 | 7/2003 | Terry et al. | |
| 2003/0144705 A1 | 7/2003 | Funke | |
| 2003/0144706 A1 | 7/2003 | Funke | |
| 2004/0088012 A1 | 5/2004 | Kroll et al. | |
| 2005/0070975 A1 * | 3/2005 | Zeijlemaker et al. | 607/60 |
| 2005/0215914 A1 | 9/2005 | Bornzin et al. | |
| 2006/0009810 A1 * | 1/2006 | Mann et al. | 607/17 |
| 2006/0025820 A1 | 2/2006 | Phillips et al. | |

OTHER PUBLICATIONS

Nyenhuis et al. "MRI and Implantable Medical Devices: Basic Interactions with an Emphasis on Heating." IEEE Transactions on Device and Materials Reliability. vol. 5, No. 3. Sep. 2005.*
Park et al. "Calculation of MRI-Induced Heating of an Implanted Medical Lead Wire with an Electric Field Transfer Function." Jrnl of Magnetic Resonance Imaging. vol. 26: 1278-1285. Oct. 29, 2007.*
Edelson, "MRI Exams Performed Remotely Over the Internet." HealthDay News. Oct. 24, 2006.
Gimbel, J. Rod et al. "Can patients with implantable pacemakers safely undergo magnetic resonance imaging?" J. Am. Coll. Cardiol. 2004;43:1325-1327.
Gimbel, J. Rod et al. "Outcome of Magnetic Resonance Imaging (MRI) in Selected Patients with Implantable Cardioverter Defibrillators (ICDs)." PACE 2005;28:270-273.
Gimbel, J. Rod et al. "Strategies for the Safe Magnetic Resonance Imaging of Pacemaker-Dependent Patients" PACE 2005;28:1041-1046.

(Continued)

*Primary Examiner* — Carl H Layno
*Assistant Examiner* — Luther Behringer

(57) ABSTRACT

Systems and methods are provided for allowing an implantable medical device, such as pacemaker, to properly sense electrophysiological signals and hemodynamic signals within a patient during a magnetic resonance imaging (MRI) procedure. Systems and methods are also provided for allowing the implantable medical device to transmit the sensed data to an external monitoring system during the MRI procedure so that attending medical personnel can closely monitor the health of the patient and the operation of the implantable device during the MRI. These improvements provide the attending personnel with information needed to determine whether the MRI should be suspended in response to induced tachyarrhythmias or other adverse conditions within the patient.

9 Claims, 10 Drawing Sheets

OTHER PUBLICATIONS

Invivo Research, "Invivo Precess MRI Vital Signs Monitor." Described at http://www.roxon.ca/prod_list.asp? Category_ID=67.

Luechinger, Roger et al. "In vivo heating of pacemaker leads during magnetic resonance imaging." Euro Heart J. 2005;26:376-383.

* cited by examiner

SYSTEMS AND METHODS FOR REMOTE MONITORING OF SIGNALS SENSED BY AN IMPLANTABLE MEDICAL DEVICE DURING AN MRI

CROSS-REFERENCE TO RELATED APPLICATIONS

This application is related to U.S. patent application Ser. No. 10/973,862, filed Oct. 25, 2004, entitled "Electromagnetic Interference Safe Modes for Implantable Electronic Devices", now abandoned, which is fully incorporated by reference herein, including the appendices thereof.

FIELD OF THE INVENTION

The invention generally relates to implantable medical devices, such as pacemakers or implantable cardioverter/defibrillators (ICDs), and to external diagnostics systems for use therewith and, in particular, to techniques for monitoring and displaying electrophysiological signals and hemodynamic signals sensed within a patient by an implantable medical device during a magnetic resonance imaging (MRI) procedure.

BACKGROUND OF THE INVENTION

MRI is an effective, non-invasive magnetic imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnetic that generates a powerful static magnetic field. The static magnetic field causes protons within tissues of the body to align with an axis of the static field. A pulsed radio-frequency (RF) magnetic field is then applied causing the protons to begin to precess around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

A significant problem with MRI is that its strong magnetic fields can interfere with the operation of any medical devices, particularly pacemakers or ICDs, implanted within the patient. Typically, pacemakers and ICDs include pulse generators for generating electrical pacing pulses and shocking circuits for generating stronger defibrillation shocks. A set of conductive leads connect the pulse generators and shocking circuits to electrodes implanted within the heart. An individual pacing pulse is applied by using the pulse generators to generate a voltage difference between a pair of the electrodes, such as between a tip electrode implanted within the right ventricle and the pacemaker housing or "can." A defibrillation shock is applied by using the shocking circuits to generate a much larger voltage difference between a pair of the electrodes, such as between a large coil electrode implanted within the right ventricle and the pacemaker housing. The leads may also have a variety of sensors for sensing physiological signals within the heart of the patient, such as pressure sensor, temperature sensors, $SvO_2$ sensors, PPG and the like. The sensors are typically connected to the implantable device via electrical signal conduction paths within the various leads so as to receive control signals from the implanted device and to relay sensed signals back to the device. The pulse generators, shocking circuits, leads, electrodes and sensors, as well as the tissue and fluids between the electrodes and sensors, collectively provide various conduction loops. State of the art pacemakers and ICDs exploit lead systems having numerous electrodes and sensors, thus presenting numerous possible conduction paths.

When patients with pacers or ICDs are exposed to MRI fields, RF fields of the MRI can induce currents along the conduction paths causing excessive current to flow into tissue or blood through tip or ring electrodes resulting in Joule heating. Excessive power dissipation might damage the tissues around pacing electrodes causing inappropriate sensing and pacing and posing risks to the patient. Additionally, the powerful gradient fields of an MRI system can induce currents among the conduction paths sufficient to trigger rapid, unwanted pacing pulses or even defibrillation shocks. These induced currents are referred to as parasitic currents. Rapid pacing pulses induced by the MRI could, in certain cases, cause a life-threatening fibrillation of the heart. Likewise, any defibrillation shocks triggered by the presence of the MRI fields can also induce fibrillation, particularly if the shock is delivered during a repolarization period of the ventricular myocardium. Another significant concern is that the induced voltages can be mistakenly sensed by the pacemaker as intrinsic heartbeats. In some pacing modes, particularly demand-based modes, the pacemaker then assumes that the heart needs no pacing assistance and will block its pacing output (i.e. delivery of a pacing pulse is inhibited.) This could cause a "pacing dependent" patient to pass out and possibly die.

In view of these concerns, various safeguard techniques have been developed that operate to detect the strong fields associated with an MRI and then switch sensing modes or pacing modes in response thereto. See, for example, U.S. Patent Application 2003/0083570 to Cho et al.; U.S. Patent Application 2003/0144704 to Terry et al.; U.S. Patent Application 2003/0144705 to Funke; U.S. Patent Application 2003/0144706 also to Funke; U.S. Pat. No. 6,795,730 to Connelly, et al., and U.S. Patent Application 2004/0088012 of Kroll et al.

However, it would be preferable to allow the implanted device to continue to operate in its normal pacing modes even during an MRI procedure, so long as heating criteria is met, arrhythmias are not induced, unnecessary pacing pulses or shocks are not delivered, and any necessary therapy is not improperly inhibited. That is, it would be desirable to allow the device to continue to monitor the heart of the patient for arrhythmias or other medical conditions even during an MRI procedure and to deliver therapy as needed and to transmit signals to deactivate the MRI system only if absolutely necessary. With such a system, it would also be desirable to control the device to transmit monitoring and diagnostic information during the MRI procedure to an external monitoring and control system so that medical personnel can monitor the status the implanted device and the health of the patient during the MRI procedure. The medical personnel then could deactivate the MRI system if warranted or adjust its operation if needed. The medical personnel could also re-program the operation of the implanted device during the MRI procedure, if appropriate. The implanted device would preferably also monitor for any arrhythmias or other abnormal medical conditions induced by the MRI fields and send appropriate signals to the MRI system to automatically deactivate the MRI system. In particular, the device would monitor for any tachyarrhythmias induced by the MRI fields so that the MRI system can be promptly deactivated and appropriate therapy delivered.

With conventional implantable systems, though, the strong MRI fields can prevent the implanted device from reliably sensing signals from the various electrodes of the leads and from the various physiological sensors, thus preventing the implanted device from reliably detecting arrhythmias or other abnormal conditions within the patient during the MRI procedure. Accordingly, there is a need to provide improved implantable components configured to allow the implanted device to continue to reliably receive signals from sensing leads and physiological sensors during an MRI and it is to this end that certain aspects of the invention are directed. Moreover, the strong MRI fields can also prevent the implanted device from reliably sending transmissions to, and receiving signals from, an external system, thus preventing the implanted device from reliably sending diagnostics data and warning signals to the external system during the MRI procedure and possibly also preventing the external system from transmitting re-programming commands to the implanted device during the MRI procedure. Accordingly, there is also a need to provide improved implantable components and external components sufficient to allow the implanted device and the external system to reliably communicate with one another during an MRI procedure and it is to this end that other aspects of the invention are directed.

Still another significant concern is that the MRI fields can cause tip electrodes of the leads to become significantly heated, potentially damaging adjacent tissues. Techniques have been developed for detecting the heating of tip electrodes and deactivating the MRI system in response thereto. See, for example, U.S. Patent Application 2006/0025820, of Phillips et al., entitled "Integrated System and Method for MRI-safe Implantable Devices." Typically, though, the implanted device merely determines whether the tip temperature has exceeded a threshold and sends signals to deactivate the MRI system. It would be preferable to additionally track changes in tip temperatures so as to provide other diagnostic information and, in particular, to exploit changes in tip temperature to determine the amount of current induced in a given lead by the MRI fields. It is to this end that still other aspects of the invention are directed.

SUMMARY

In accordance with a first general embodiment, methods are provided for use by an implantable medical device for implant within a patient, wherein the method is for use during an MRI procedure. In one example, signals are sensed within the patient during the MRI procedure while filtering the sensed signals to reduce the influence of MRI fields on the sensed signals and then the signals are transmitted to an external monitoring system during the MRI procedure so that the signals can thereby be remotely monitored during the MRI. The signals sensed by the implanted device and then transmitted to the external system include electrophysiological signals such as intracardiac electrogram (IEGM) signals. The signals sensed by the device and then transmitted to the external system can also include hemodynamic signals such as: intracardiac pressure signals, blood oxygen saturation signals, blood temperature signals, and photoplethysmography (PPG) signals. Device diagnostic signals can also be transmitted to the external system, such as signals representative of tip temperatures or induced currents. By providing all or at least some of these signals to the external monitoring system during the MRI, medical personnel can thereby closely monitor the health of the patient and the operation of the implantable device during the MRI, hence providing the attending medical personnel with information needed to determine whether the MRI should be suspended in response to induced tachyarrhythmias or other adverse conditions within the patient.

In an exemplary embodiment, the electrophysiological and hemodynamic signals sensed by the implantable device are filtered using filters configured to reduce the influence of MRI fields on the sensed signals, such as by filtering the signals at frequencies associated with MRI fields. For example, 64 megahertz (MHz) and 128 MHz notch filters may be provided within terminals of the implanted device that receive signals from sensing/pacing leads and within terminals of the implanted device that receive signals from additional physiological sensors. The notch filters substantially eliminate any signal components arising at the MRI frequencies from entering the sensing circuitry within the implanted device, thus allowing the device to more reliably sense electrophysiological and hemodynamic signals even while MRI fields are being applied. Additionally, or alternatively, adaptive slew rate filters are provided for filtering signals at slew rates associated with MRIs, such as slew rates in the range of 100 milliTesla per meter per millisecond (mT/m/ms) to about 400 mT/m/ms. In some embodiments, it may be appropriate to also provide notch filters and/or slew rate filters within the leads or sensors themselves, particularly within any physiological sensors that receive command and control signals from the implantable device.

In the exemplary embodiment, any signals to be transmitted to the external monitoring system during the MRI procedure are transmitted at frequencies associated with medical implant communication services (MICS) band frequencies, particularly frequencies in the range of 402 MHz-405 MHz. Alternatively, the signals are transmitted at frequencies associated with industrial scientific medical (ISM) band frequencies, particularly frequencies in the range of about 2.5 GHz-5.0 GHz. By transmitting signals at MICS band or ISM band frequencies, the implantable device can more reliably transmit the electrophysiological and hemodynamic signals, and any other diagnostic signals, to the external monitoring system during the MRI procedure for display. Medical personnel can then review the information received from the implantable device to verify that the implantable device is operating safely within the patient and to deactivate the MRI system if necessary or to re-program the operation of the implantable device, if warranted. In implementations where the external system is equipped to re-program or otherwise adjust the operation of the implantable device during the MRI procedure, MICs band or ISM band frequencies can also be used to transmit the appropriate programming signals to the device under the control of the attending medical personnel.

In addition to relaying electrophysiological and hemodynamic signals to the external monitoring system, the implantable device also preferably analyzes the sensed signals to detect any abnormal conditions within the patient such as arrhythmias, abnormal patient blood temperatures and abnormal patient blood pressures. Upon detection of any abnormal conditions, appropriate warning signals are sent to the external monitoring system for review by the medical personnel. Warnings pertaining to tachyarrhythmias are responded to immediately by attending personnel by, e.g., removing the patient from the MRI and promptly delivering any needed therapy.

Depending upon the nature of the arrhythmia, the device may also automatically change its pacing mode in response to the arrhythmia. Likewise, depending upon the nature of the arrhythmia, the external monitoring system, upon reception of the warning signals, may automatically deactivate the MRI system. Still further, the external monitoring system may analyze the various electrophysiological and hemodynamic signals received from the implantable device to detect any abnormal conditions that the device may not have detected and to generate warning signals accordingly. In this regard, more sophisticated analysis procedures may be employed by the external system to detect arrhythmias, i.e. analysis procedures that the implantable device may not have the resources to perform. Should an arrhythmia be detected, the MRI is deactivated and appropriate therapy is immediately delivered by the attending personnel.

Preferably, temperature sensors are provided within the various leads from which the implantable device can detect any abnormally high tip temperatures so that appropriate warning signals can be sent to the external monitoring system or to the MRI system itself. Still further, the implantable device preferably tracks temperature profiles for one or more of the tip electrodes, i.e. changes in tip temperature over time during MRI scans, from which either the device or the external monitoring system can determine the amount of current induced within the leads. Appropriate warning signals can be generated or other actions taken in response to any induced currents that exceed a predetermined acceptable threshold.

Preferably, the aforementioned procedures performed by the implantable device are initiated prior to the initiation of the MRI procedure so as to provide medical personnel with "baseline" electrophysiological and hemodynamic signals obtained within the patient before the MRI procedure for comparison against subsequent signals obtained during the MRI. In one example, the external monitoring system transmits a suitable MRI system notification signal, which the implantable device is equipped to detect. In this manner, the implantable device can detect entry into the MRI procedure room and promptly initiate an MRI operational mode where the aforementioned signals filtering and transmission procedures are performed. Alternatively, the external monitoring system or an external programmer device may be used by medical personnel within the MRI procedure room to manually re-program the implantable device to switch to the MRI operational mode.

Although thus far summarized primarily with reference to the operations performed by the implantable medical device during an MRI procedure, it should be understood that aspects of the invention may be implemented partially or exclusively within external systems. That is, in accordance with a second general embodiment of the invention, methods are provided for use by an external monitoring system used in conjunction with an implantable medical device for implant within a patient. Briefly, signals are received by the external monitoring system via long-range telemetry during a magnetic imaging procedure that had been transmitted from an implantable medical device implanted within a patient undergoing the procedure. The signals, which may include electrophysiological and hemodynamic signals, are received at frequencies selected to reduce the influence of magnetic imaging fields on the transmitted signals. The external monitoring system processes the received signals during the imaging procedure, such that signals sensed within the patient during the procedure can be remotely monitored during the procedure. As already explained, such processing can include displaying the received signals, analyzing the signals to detect abnormal conditions within the patient, etc. Additionally, tip temperature signals, induced current signals, device diagnostics, and various warnings can be received and displayed by the external monitoring system. Warnings pertaining to tachyarrhythmias are responded to immediately by attending personnel by, e.g., removing the patient from the MRI and promptly delivering any needed therapy.

Any or all of the various electrophysiological and hemodynamic signals, tip temperature signals, induced current signals, device diagnostics, warnings and the like can be forwarded from the external monitoring system, which is preferably mounted near the MRI system, to a remote monitoring terminal for review by other medical personnel. For example, the various signals and warnings can be selectively forwarded via the Internet to a cardiologist or electrophysiologist at a remote location. In particular, if any abnormal conditions arise within the patient that the personnel operating the MRI system are unable to diagnose, appropriate diagnostic data can thereby be promptly forwarded to an expert who can then recommend appropriate action. However, the forwarding of data for remote review is not performed in lieu of removing a patient from the MRI in response to a tachyarrhythmia. Rather, any serious arrhythmia is addressed immediately by the MRI personnel. Nevertheless, circumstances may arise where it is desirable to have IEGMs or other diagnostic data reviewed by experts at a remote location, time permitting.

The invention is perhaps most advantageously implemented for use with MRI systems but principles of the invention may be exploited for use with other systems providing strong magnetic fields as well.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI-Responsive Systems and Procedures

Figure 1:
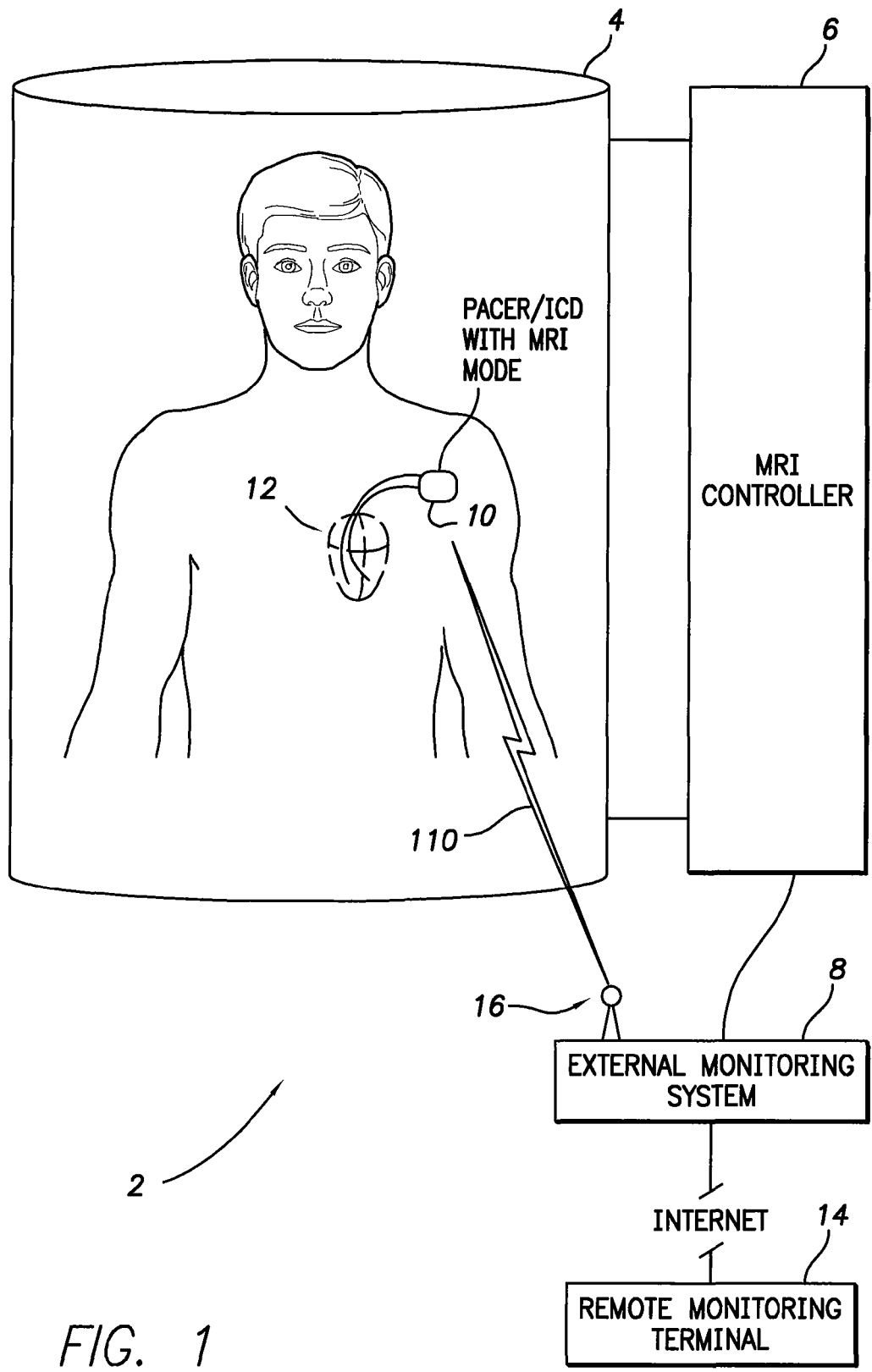
FIG. 1 is a stylized representation of an MRI system along with a patient with a pacer/ICD implanted therein that is capable of communicating with an external monitoring system during an MRI procedure.
Figure 9:
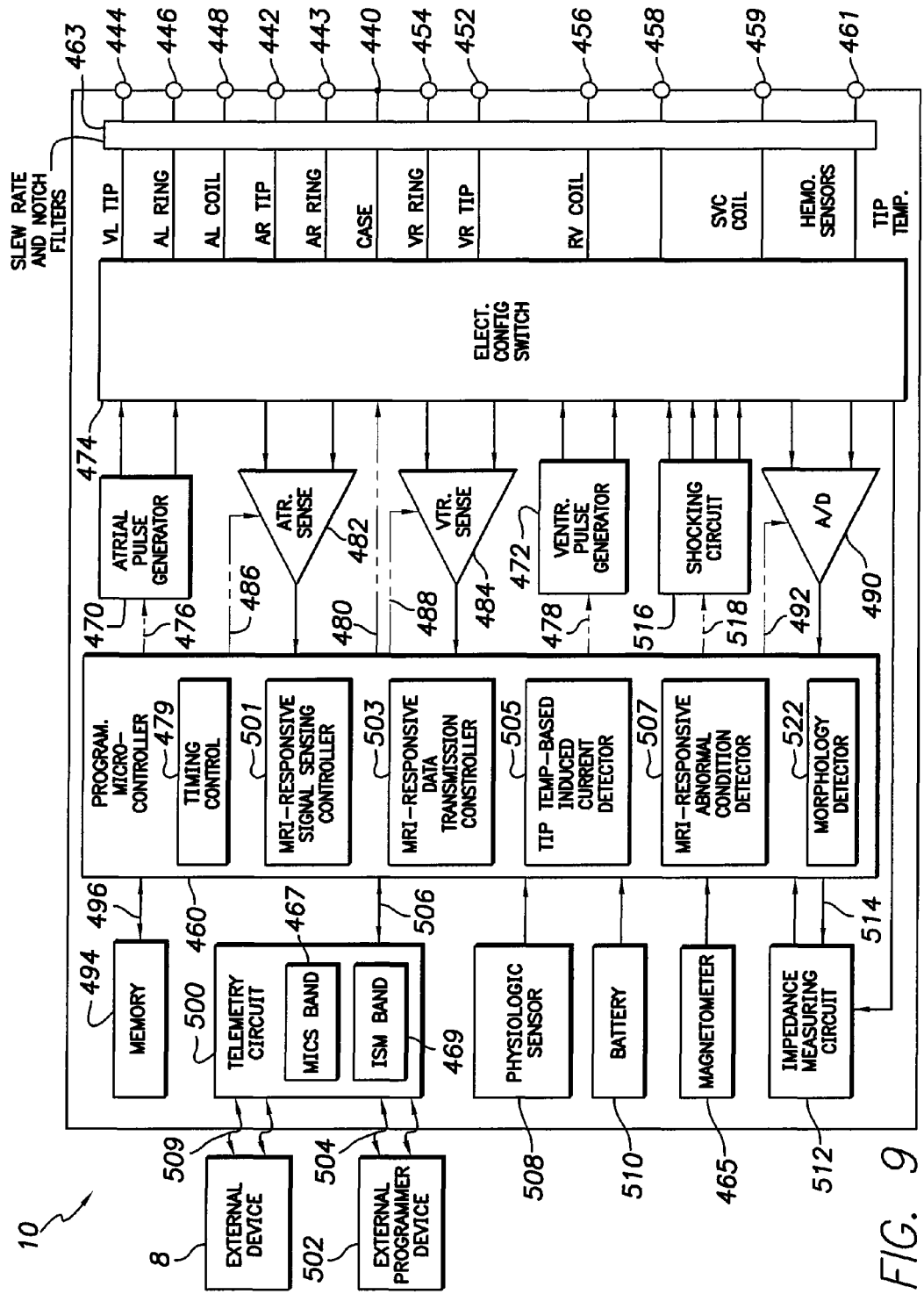
FIG. 9 is a functional block diagram of the pacer/ICD of FIG. 8, illustrating basic circuit elements that provide cardioversion, defibrillation and/or pacing stimulation in four chambers of the heart and particularly illustrating components for MRI-mode processing.

FIG. 1 illustrates an overall MRI system 2 having an MRI machine 4 operative to generate MRI fields during an MRI procedure for examining a patient. The MRI machine operates under the control of an MRI controller 6, which controls the strength and orientation of the fields generated by the MRI machine and derives images of portions of the patient therefrom, in accordance with otherwise conventional techniques. MRI machines and imaging techniques are well known and will not be described in detail herein. See, for example, U.S. Pat. No. 5,063,348 to Kuhara, et al., entitled "Magnetic Resonance Imaging System" and U.S. Pat. No. 4,746,864 to Satoh, entitled "Magnetic Resonance Imaging System." An external monitoring system 8 is also provided that communicates via long range RF telemetry during the MRI procedure with a pacer/ICD 10 implanted within the patient to receive transmissions of electrophysiological signals and/or hemodynamic signals sensed within the patient by the pacer/ICD during the MRI procedure, as well as other diagnostic data to be described in greater detail below. A lead system 12 is coupled to the pacer/ICD for sensing electrophysiological signals within the heart of the patient, such as A-IEGM and V-IEGM signals, and for delivering any needed pacing pulses or shock therapy. In FIG. 1, only two leads are shown. A more complete lead system is illustrated in FIG. 9, described below. In general, any of the electrophysiological signals sensed using the pacing/sensing leads might potentially be transmitted to the external monitoring system during the MRI procedure for display thereon.

The lead system may also include various physiological sensors (not separately shown within FIG. 1) for sensing hemodynamic signals or other signals within the patient, such as sensors operative to sense intracardiac pressure, blood oxygen saturation (i.e. blood $SO_2$), blood temperature, and PPG signals, etc. In some cases, the sensors may be implanted elsewhere in the patient or may be mounted in or on the pacer/ICD itself. In any case, any of the various hemodynamic signals or other signals sensed using the sensors might potentially be transmitted to the external monitoring system during the MRI procedure for display thereon. Also, as will be further explained, during the MRI procedure, the pacer/ICD also analyzes the various sensed signals to detect abnormal conditions such as tachyarrhythmias, sudden drops in blood pressure, sudden changes in blood temperature, etc. Warning signals pertaining to any such abnormal conditions may also be transmitted from the pacer/ICD to the external monitoring system during the MRI procedure for review. Still further, the lead system is preferably equipped with one or more temperature sensors (not shown in FIG. 1) for detecting tip temperatures from which the pacer/ICD estimates the amount of electrical current, if any, induced within the leads by the MRI fields. Warnings and other information pertaining to tip temperatures or induced currents may also be transmitted to the external monitoring system during the MRI procedure for review. Depending upon the nature of the warning, the external monitoring system may deactivate the MRI machine by sending appropriate control signals to the MRI controller. Alternatively, medical personnel operating the system may manually deactivate the MRI machine in response to the warnings by using an MRI control interface, not separately shown.

External monitoring system 8 is also preferably equipped to analyze any of the various signals received from the pacer/ICD to detect abnormal conditions, including abnormal tip temperatures, abnormal induced current levels, tachyarrhythmias, etc., and to generate suitable warning signals for the attending personnel and to directly deactivate the MRI, if appropriate. In particular, the external monitoring system may be provided with more sophisticated software or hardware than included within the pacer/ICD itself, for use in analyzing IEGMs, cardiac pressure signals, and the like to detect abnormal conditions. In this regard, the external monitoring system may be provided with software requiring greater memory or processing resources than available within the pacer/ICD. Where appropriate, information received or generated by the external monitoring system is forwarded via the Internet or other appropriate communications network to a remote monitoring terminal 14 for review thereon. In particular, IEGMs corresponding to any abnormal cardiac conditions that neither the external monitoring system nor the attending personnel are able to diagnose may be forwarded to the remote monitor for review by an electrophysiologist or cardiologist with greater expertise.

To permit communication with the pacer/ICD during the MRI procedure, the external monitoring system includes an RF telemetry antenna 16 that communicates via MICS or ISM channels with corresponding RF telemetry components within the pacer/ICD (shown in FIG. 9, discussed below). Preferably, the RF telemetry antenna of the external monitoring system also periodically emits suitable MRI notification signals at all times. The pacer/ICD is equipped to sense such notification signals to thereby detect entry of the patient into the MRI procedure room. Upon detection of such entry, the pacer/ICD switches to an MRI mode wherein the pacer/ICD activates various filtering procedures (to be discussed below) for use in the presence of MRI fields and also promptly begins transmitting IEGMs and other signals of interest via MICS or ISM frequencies to the external monitoring system for display thereon, so as to provide baseline signals for comparison against signals subsequently transmitted during the MRI procedure. The pacer/ICD continues to operate in the MRI mode throughout the MRI procedure and does not switch back to normal processing modes until the patient has eventually been removed from the MRI procedure room, as detected based on loss of reception of the periodic notification signals.

Figure 2:
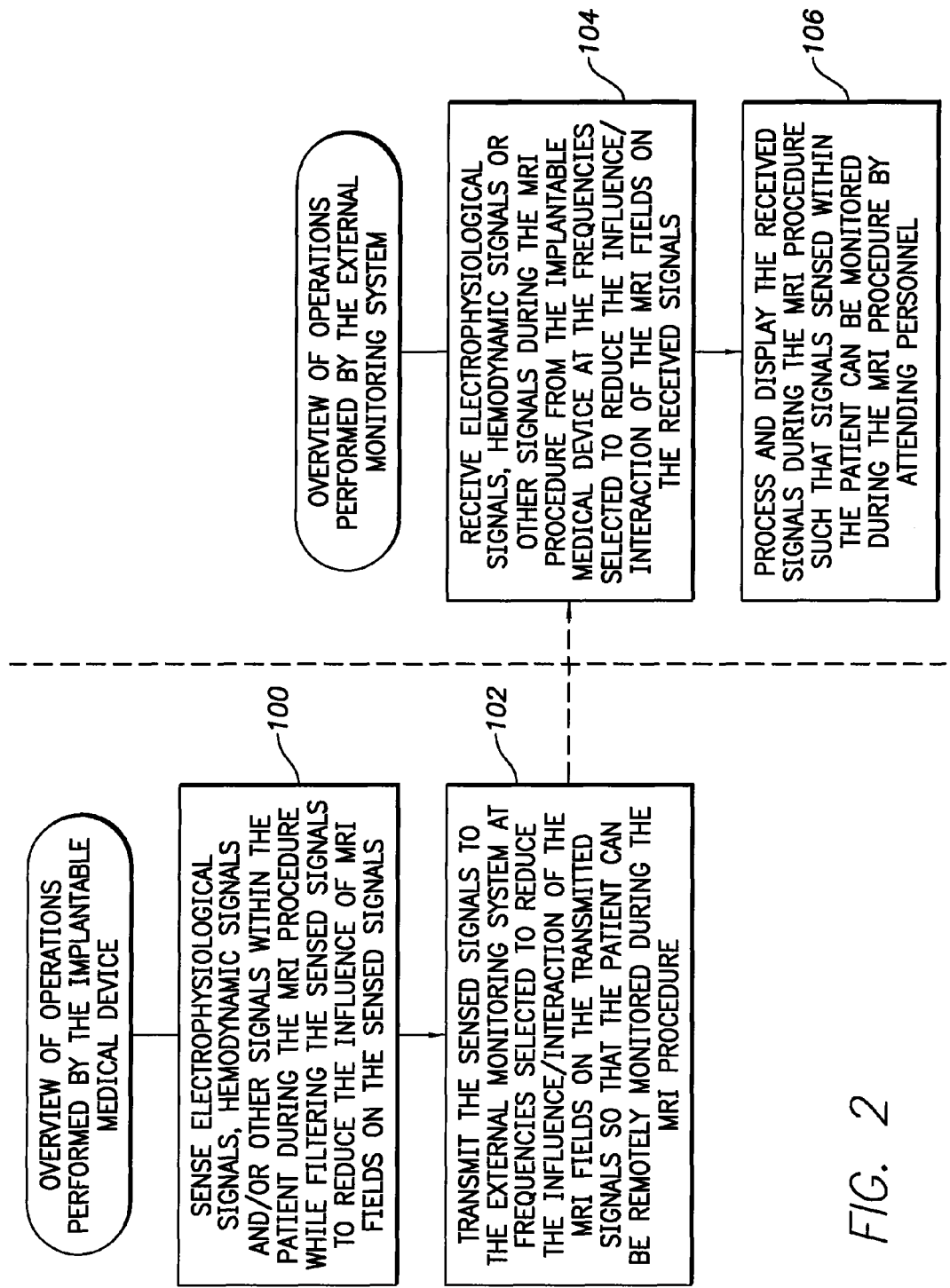
FIG. 2 is a flow diagram providing a broad overview of techniques performed by the pacer/ICD and the external monitoring system of FIG. 1.

FIG. 2 broadly summarizes the operations performed by the pacer/ICD and the external monitoring system of FIG. 1 while in the MRI mode. Briefly, beginning at step 100, the pacer/ICD senses electrophysiological signals, hemodynamic signals and/or other signals within the patient during the MRI procedure, while filtering the sensed signals to reduce the influence of MRI fields on the sensed signals. At step 102, the pacer/ICD transmits the sensed signals to the external monitoring system during the MRI procedure at frequencies selected to reduce the influence of the MRI fields on the transmitted signals so that the patient can be remotely monitored during the MRI procedure. At step 104, the electrophysiological signals, hemodynamic signals and/or other signals transmitted by the pacer/ICD during the MRI procedure are received by the external monitoring system at the frequencies selected to reduce the influence of the MRI fields on the signals and/or the interaction of the signals with the fields. At step 106, the external monitoring system processes and displays the received signals during the MRI procedure, such that signals sensed within the patient can be monitored during the MRI procedure by attending personnel.

Illustrative MRI-Responsive Systems and Procedures

FIGS. 3-7 set forth illustrative embodiments of the invention. Operations performed by the pacer/ICD are set forth in FIGS. 3-5; operations performed by the external monitoring system or other external systems are set forth in FIGS. 6-7.

Figure 3:
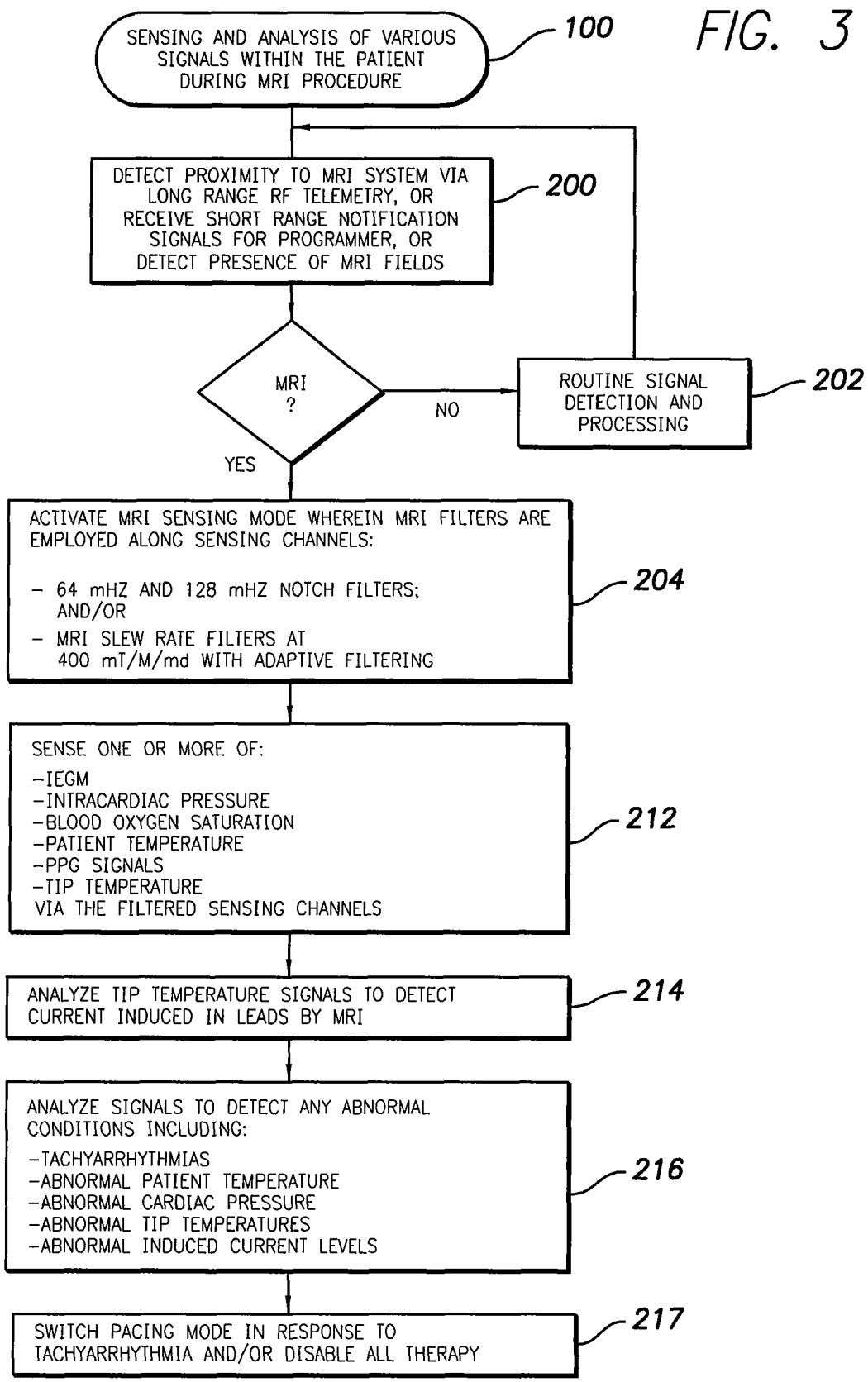
FIG. 3 is a flow diagram providing a more detailed illustration of exemplary processing techniques in accordance with the general techniques of FIG. 2, particularly signal sensing and filtering procedures performed by the pacer/ICD during an MRI procedure.

FIG. 3 illustrates exemplary techniques that may be performed by the pacer/ICD in accordance with step 100 of FIG. 2. Beginning at step 200, the pacer/ICD (1) detects the proximity to an MRI system via long-range RF telemetry, (2) receives short-range notification signals from a device programmer notifying it of the MRI, or (3) directly detects the presence of MRI fields. As noted, the external monitoring system preferably transmits notification signals periodically via MICs band or ISM band long-range telemetry, which the pacer/ICD is equipped to sense, so as to detect entry of the patient into an MRI procedure room. MICS band frequencies are in the range of 402 MHz-405 MHz. ISM band frequencies are in the range of 2.5 GHz-5.0 GHz. Upon detection of the MRI notification signals, the pacer/ICD automatically switches to an MRI mode of operation where, as will be explained, it begins to sense signals subject to special MRI filtering procedures, analyzes the signals accordingly, and begins transmitting the signals to the external monitoring system for review, etc. If the external monitoring system is not equipped to transmit such notification signals, or if the pacer/ICD is not equipped to receive and respond to those notification signals, the pacer/ICD can nevertheless be switched to the MRI mode of operation based on short-range telemetry signals received from a device programmer. That is, the pacer/ICD of the patient may be re-programmed by a standard device programmer, using otherwise conventional programming techniques, to switch to the MRI mode before the patient is placed in the MRI machine. (Note that the device programmer may also be equipped to perform all the functions of the external monitoring system, so that separate device programmers and external monitoring systems are not necessarily required.) If the pacer/ICD is not, for whatever reason, switched to the MRI mode prior to initiation of the MRI procedure, the pacer/ICD nevertheless detects the presence of the MRI fields using, e.g., suitable magnetic field sensors installed within the pacer/ICD, and automatically switches to the MRI mode.

So long as no MRI notification signals, programming signals, or MRI fields are sensed, normal processing is performed by the pacer/ICD, at step 202. By "normal" processing, it is meant that the pacer/ICD performs functions in a manner that does not specifically take into account the presence of strong magnetic fields. For a pacer/ICD, normal functions involve any of a variety of cardiac rhythm management functions, such as anti-bradycardia pacing, anti-tachycardia pacing (ATP), overdrive pacing, and the like, that involve delivering electrical stimulation to heart tissue using otherwise conventional sensing and analysis techniques. For other implantable medical devices, such as neural stimulators or the like, normal processing may involve the delivery of electrical stimulation to nerves or other tissues, again in a manner that that does not specifically take into account the presence of strong magnetic fields.

Assuming, however, that the pacer/ICD is switched to the MRI mode, then step 204 is performed wherein the pacer/ICD activates an MRI sensing mode where MRI filters are employed along sensing channels, including 64 MHz and 128 MHz notch filters and/or MRI slew rate filters operating in the range of 100 mT/m/ms to about 400 mT/m/ms with, preferably, adaptive filtering. As far as the notch filters are concerned, such filters may be permanently mounted within feedthrough filters provided at each input terminal, preferably including each pacing/sensing lead feedthrough and each physiological sensor lead feedthrough. (Feedthrough filters are discussed in, e.g., U.S. patent application Ser. No. 11/256,480, now abandoned filed Oct. 20, 2005, of Propato et al., entitled "Improved Feedthrough Filter for Use in an Implantable Medical Device." See, also, U.S. patent application Ser. No. 11/450,945, now abandoned filed Jun. 9, 2006, of Propato, entitled "Multilayer L-section Filter for use in an Implantable Medical Device.") That is, the notch filters continuously filter input signals, whether in the MRI mode or not. However, in other implementations, the notch filters may be configured so as to be activated or inserted along the signals lines only during the MRI mode. Notch filters may also be mounted at the input terminals of any physiological sensors that receive command or control signals from the pacer/ICD, particularly any sensors that preferably operate even during an MRI, such as cardiac pressure sensors. In any case, the various notch filters substantially eliminate signals at 64 MHz and 128 MHz, which are the typical operating frequencies of MRI systems, and hence the filters substantially eliminate any components of sensed signals that might be caused by the MRI, rather than by the electrophysiological and/or hemodynamic phenomena of interest. In particular, by filtering out MRI signals from electrophysiological and/or hemodynamic signals, the pacer/ICD will not erroneously respond to the MRI signals and will respond instead only to the underlying signal of interest.

Insofar as the slew rate and/or adaptive filters are concerned, such filters are preferably activated only within the MRI mode. Again, such filters may be provided at all input signal feedthroughs, both within the pacer/ICD and within any physiologic sensors, particularly those that are intended to operate even during an MRI. Slew rate filters are discussed in, e.g., U.S. Pat. No. 6,052,614 to Morris et al., "Electrocardiograph Sensor and Sensor Control System for Use with Magnetic Resonance Imaging Machines." See, also, U.S. Pat. No. 7,039,455 to Brosovich, et al., "Apparatus and Method for Removing Magnetic Resonance Imaging-Induced Noise from ECG Signals." Adaptive filtering techniques can be additionally or alternatively be applied. See, for example, U.S. Pat. No. 6,675,036 to Kreger, et al., entitled "Diagnostic Device Including a Method and Apparatus for Bio-Potential Noise Cancellation Utilizing the Patient's Respiratory Signal." The aforementioned patents generally pertain to the filtering of ECG signals but such filtering techniques can be applied, where appropriate, to the filtering of IEGM signals, physiological signals, etc.

Figure 4:
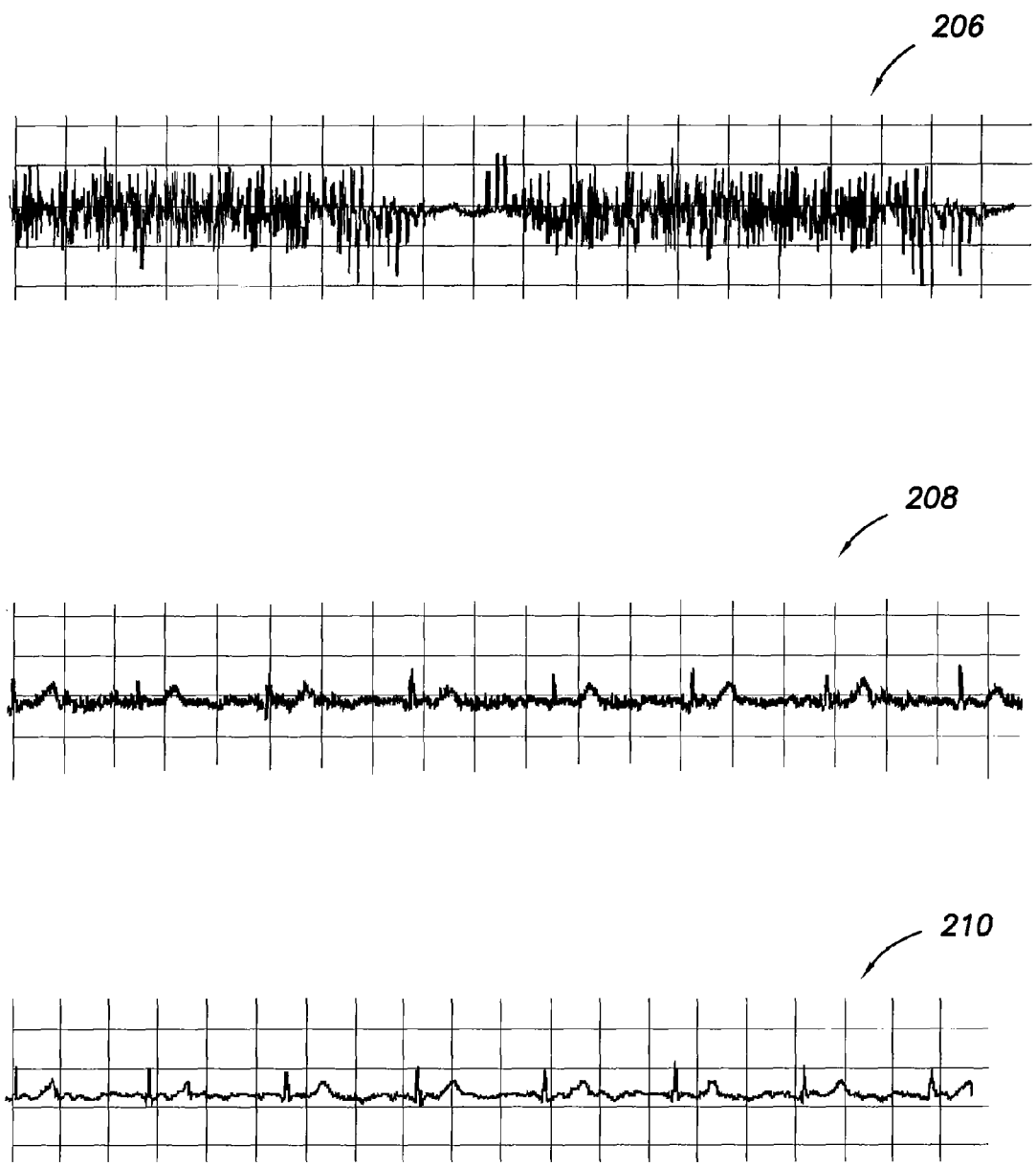
FIG. 4 is a graph illustrating the efficacy of filtering techniques performed by the pacer/ICD of FIG. 1 during an MRI procedure.

FIG. 4 illustrates the effectiveness of slew rate filters and adaptive filters. A first graph 206 illustrates an IEGM in the presence of MRI noise. A second graph 208 illustrates the same IEGM, filtered using a slew rate filter set based on the characteristics of the MRI. As can be seen, the IEGM is more clearly presented. A third graph 210 illustrates the same IEGM, additionally filtered using an adaptive filter. The IEGM is even more clearly presented.

Returning to FIG. 3, at step 212, the pacer/ICD senses one or more of: IEGM signals, such as separate A-IEGM and V-IEGM channels; intracardiac pressure signals, such as left atrial pressure (LAP), right ventricular pressure (RVP); blood oxygen saturation signals, such as separate venous oxygen saturation ($SvO_2$) and arterial oxygen saturation ($SaO_2$) signals; patient temperature values, such as blood temperature or body temperature; PPG signals; and tip temperature values. The various signals or values are sensed using the filtered sensing techniques discussed in step 204. As such, any noise with the sensed parameters due to the MRI fields is substantially reduce or eliminated. These sensed parameters are merely exemplary. A wide variety of other electrophysiological and/or hemodynamic parameters can additionally, or alternatively, be sensed. Examples include, pH values, blood glucose values, accelerometer values, stroke volume, cardiac output values, contractility values, respiration, acoustic sensor values and end diastolic volume (EDV) values.

The sensors themselves can be otherwise conventional. However, particularly effective techniques for detecting blood pressure values are discussed in U.S. patent application Ser. No. 11/378,604, now U.S. Pat. No. 7,654,964 filed Mar. 16, 2006, of Kroll et al., entitled, "System and Method for Detecting Arterial Blood Pressure based on Aortic Electrical Resistance using an Implantable Medical Device." Particularly effective techniques for detecting blood oxygen saturation values are discussed in U.S. patent application Ser. No. Ser. No. 11/387,579, filed Mar. 23, 2006, of Koh, entitled "System and Method for Calibrating a Blood Oxygen Saturation Sensor for use with an Implantable Medical Device." Particularly effective techniques for detecting stroke volume and/or cardiac output values are discussed in U.S. patent application Ser. No. 11/267,665, now abandoned filed Nov. 4, 2005, of K R et al., entitled "System and Method for Measuring Cardiac Output via Thermal Dilution using an Implantable Medical Device with Thermistor Implanted in Right Ventricle." Particularly effective techniques for detecting EDV values are discussed in U.S. Patent Publication No. 2005/0215914, to Bornzin et al., entitled "System and Method for Evaluating Heart Failure Based on Ventricular End-Diastolic Volume using an Implantable Medical Device." Particularly effective techniques for detecting contractility values are described in: U.S. Pat. No. 5,800,467 to Park et al., entitled "Cardio-Synchronous Impedance Measurement System for an Implantable Stimulation Device." Particularly effective techniques for detecting respiration are described in: U.S. patent application Ser. No. 11/100,189, now U.S. Pat. No. 7,404,799 filed Apr. 5, 2005, of Koh, entitled "System and Method for Detection of Respiration Patterns via Integration of Intracardiac Electrogram Signals." Particularly effective techniques for mounting multiple sensors to individual leads are described in U.S. patent application Ser. No. 11/623,663, filed Jan. 16, 2007, of Zou et al., entitled "Sensor/Lead Systems for use with Implantable Medical Devices." Particularly effective techniques for detecting tip temperature include placing temperature sensors on leads by winding the sensor wire so as to cancel induced current or by placing the wires inside suitable coaxial outer conductors or by using fiber optic techniques.

At step 214, the pacer/ICD then analyzes the tip temperature signals to estimate the amount of current induced in the leads. That is, for each tip electrode for which a temperature profile can be ascertained based on a series of tip temperature values detected over a period of time, the pacer/ICD estimates the current induced along the lead in which that particular tip electrode is mounted. If tip temperature values are obtained for each lead, then the pacer/ICD can estimated the current induced in each lead. In this regard, RF heating of tip electrode is closely related to the specific absorption rate (SAR) of the tip electrode material and the induced current through the lead. (SAR is defined as the RF power absorbed per unit of mass of an object, and is measured in watts per kilogram (W/kg).) Hence, induced current levels can be estimated based on tip temperatures. For example, the relationship between tip temperature and induced current for a particular lead may be established in advance via otherwise conventional techniques, e.g. linear regression, with the numerical relationship then programmed via software within the pacer/ICD. Thereafter, changes in tip temperature can be converted into induced current estimates by the pacer/ICD.

At step 216, the pacer/ICD analyze any or all of the various signals that have been sensed and any values derived therefrom to detect any abnormal conditions within the patient including: arrhythmias, such as ventricular tachyarrhythmias induced by the MRI; abnormal patient temperatures, such as abnormal blood temperatures or body temperatures; abnormal cardiac pressure values, such as sudden drops in blood pressure; abnormal tip temperatures; and/or abnormal induced current levels. In this regard, various threshold values indicative of "normal" ranges of temperature and pressure values may be preprogrammed within the pacer/ICD for comparison purposes to detect abnormal conditions. Otherwise conventional techniques for distinguishing among different types of arrhythmias may be employed. For example, a ventricular rate sensed within the patient can be compared against separate VT and VF thresholds. If the rate exceeds a higher VF threshold (set, e.g., to 220 beats per minute (bpm)), then VF is detected. If the rate only exceeds the lower VT threshold (set, e.g., to 180 bpm), then VT is detected.

At step 217, the pacer/ICD delivers suitable therapy in response to the abnormal condition. Also, in response to a ventricular tachyarrhythmia, the pacer/ICD may perform an Automatic Mode Switch (AMS), wherein the pacemaker reverts from a tracking mode such as a VDD or DDD mode to a nontracking mode such as VVI or DDI mode. VVI and DDI are standard device codes that identify the mode of operation of the device. Others standard modes include DDD, VDD and VOO. Briefly, DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. VOO identifies fixed-rate ventricular pacing, which ignores any potentially sensed cardiac signals. This mode is quite different from the aforementioned "demand" modes, which only pace when the pacemaker determines that the heart is "demanding" pacing. Numerous other device modes of operation are possible, each represented by standard abbreviations of this type. In some implementations, at step 217, the pacer/ICD might also deliver certain kinds of therapy in response to an arrhythmia. Preferably, though, any such therapy is suspended pending deactivation of the MRI machine, as the heart might revert to a normal sinus rhythm once the MRI is deactivated. Also, attempts to deliver therapy during an MRI might cause damage. For example, strong currents from cardioversion or defibrillation shocks might generate high force/torque that could damage the leads and cause severe heating. Accordingly, patients should be immediately removed from the MRI room in response to any arrhythmias. Therapy is then delivered in response to any sustained events.

Figure 5:
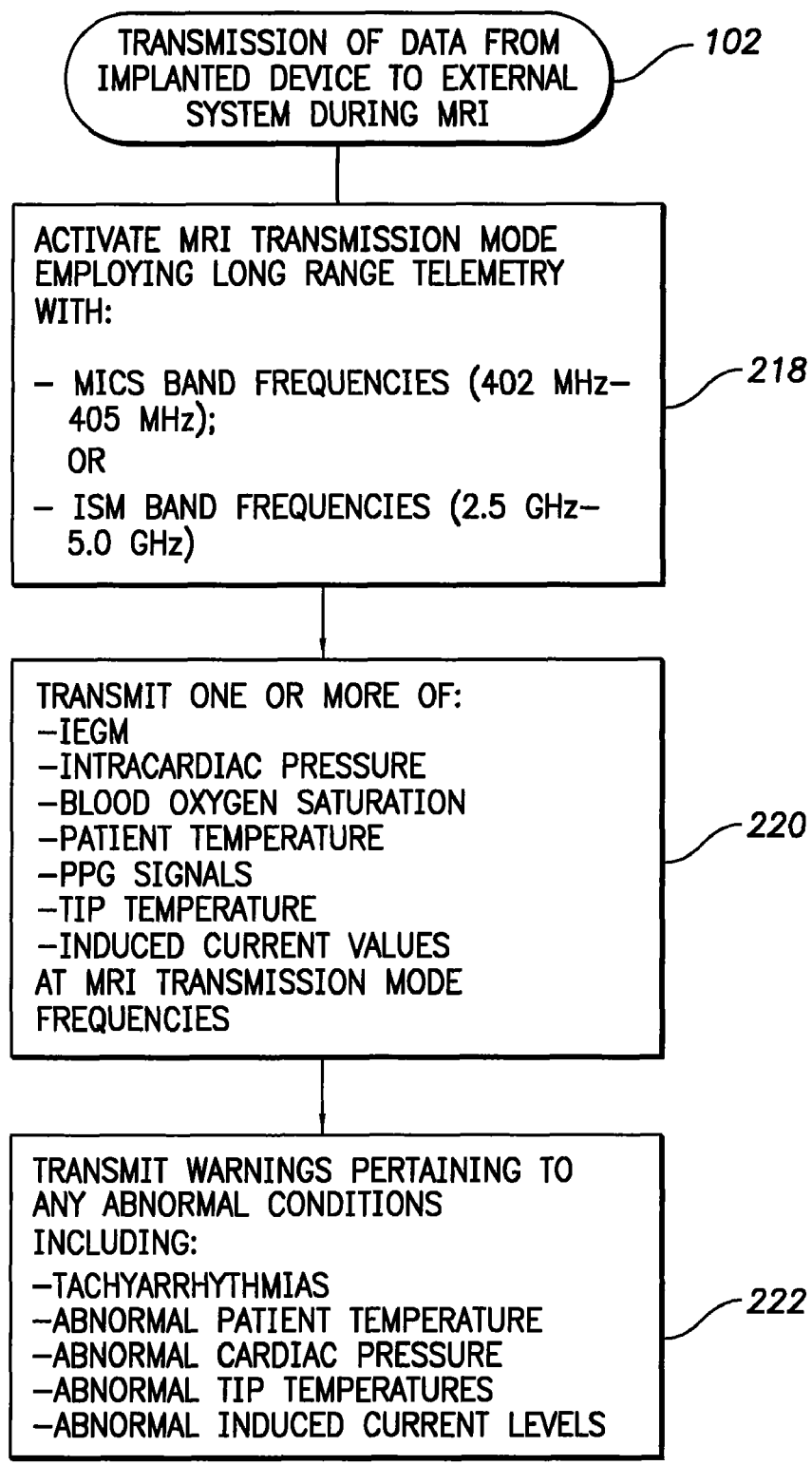
FIG. 5 is a flow diagram providing a more detailed illustration of exemplary processing techniques performed in accordance with the general techniques of FIG. 2, particularly signal transmission procedures performed by the pacer/ICD during the MRI procedure.

FIG. 5 illustrates exemplary techniques that may be performed by the pacer/ICD in accordance with step 102 of FIG. 2. Beginning at step 218, the pacer/ICD activates an MRI transmission mode employing long range RF telemetry using: MICS band frequencies (402 MHz-405 MHz) or ISM band frequencies (2.5 GHz-5.0 GHz), and any communications protocols associated therewith. That is, the telemetry components of the pacer/ICD are equipped to receive and transmit data at those frequencies and in accordance with those protocols. As already noted, by receiving/transmitting data at those frequencies, the data can be communicated without any significant noise due to the MRI. At step 220, the pacer/ICD then begins transmitting one or more of: IEGMs; intracardiac pressure values, blood oxygen saturation values, patient temperature values, PPG signals, tip temperature values, induced current values (if calculated by the device), etc., at the MRI transmission mode frequencies. Again, these parameters are merely exemplary. A wide variety of other electrophysiological and/or hemodynamic parameters can additionally, or alternatively, be transmitted, such as pH values, blood glucose values, accelerometer values, stroke volume, cardiac output values, contractility values, respiration, acoustic sensor values and EDV values. Assuming that the pacer/ICD initiates its MRI mode prior to the commencement of the MRI procedure (as discussed with reference to step 200 of FIG. 3), the pacer/ICD will be begin transmitting data prior to the commencement of the MRI procedure and the generation of MRI RF field during the procedure. Accordingly, the initial values that are sensed and transmitted will be representative of baseline values. Subsequent values sensed and transmitted during the MRI may then be compared against the baseline values by the attending personnel.

At step 222, the pacer/ICD transmits warnings pertaining to any abnormal conditions detected at step 216 of FIG. 3 including: tachyarrhythmias; abnormal patient temperature; abnormal cardiac pressure; abnormal tip temperatures and abnormal induced current levels. Any abnormal conditions detected before the initiation of the MRI procedure, such as any abnormal pressure levels or the presence of any arrhythmias, may warrant postponement of the MRI procedure. Any abnormal condition not detected until the MRI procedure commences may be due to the MRI fields and hence may warrant deactivation of the MRI machine. Any abnormal conditions persisting even after the MRI machine has been deactivated may warrant emergency attention, particularly any tachyarrhythmias that are sustained well after the MRI is deactivated.

Figure 6:
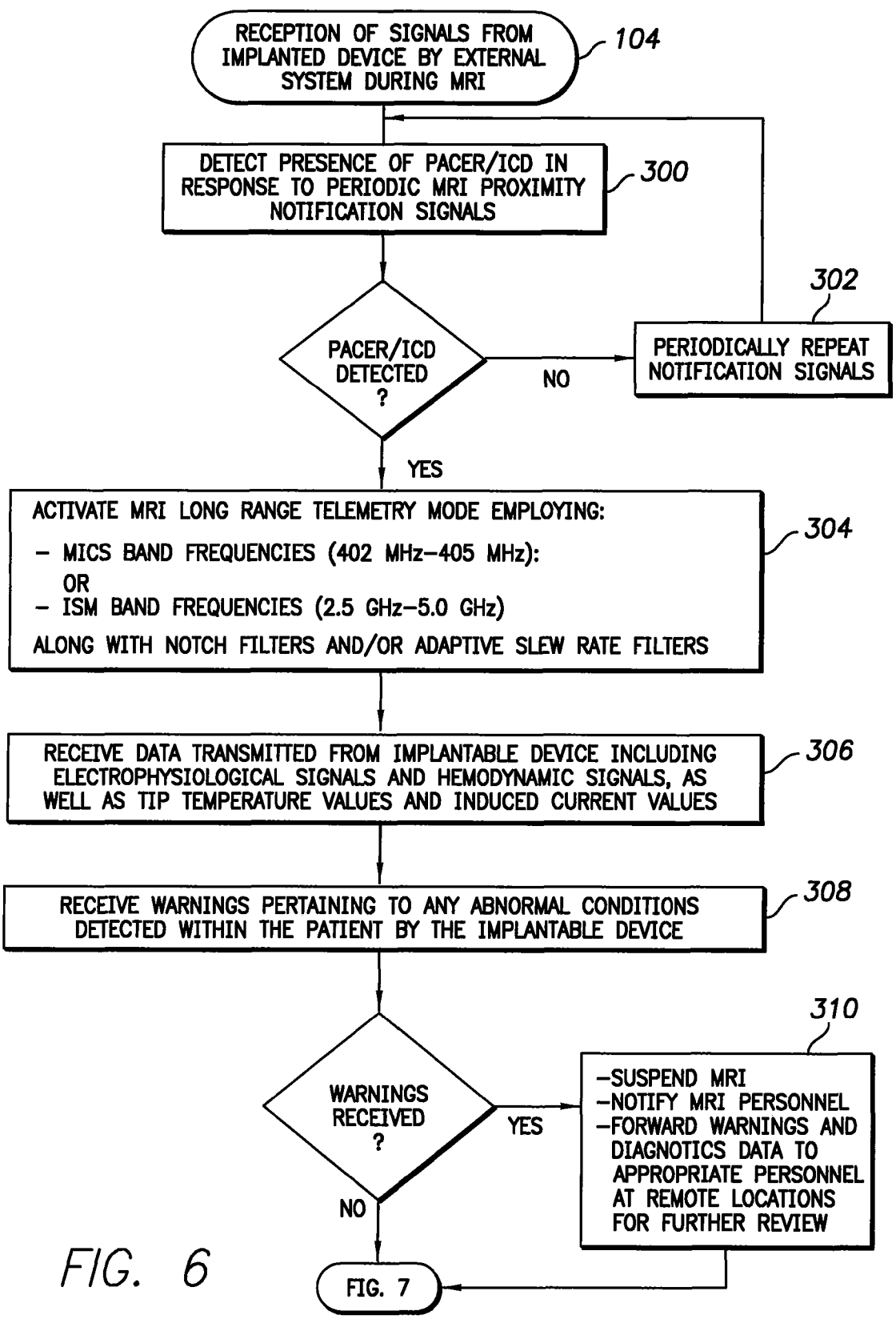
FIG. 6 is a flow diagram providing a more detailed illustration of exemplary processing techniques performed in accordance with the general techniques of FIG. 2, particularly signal reception procedures performed by the external monitoring system during the MRI procedure.
Figure 7:
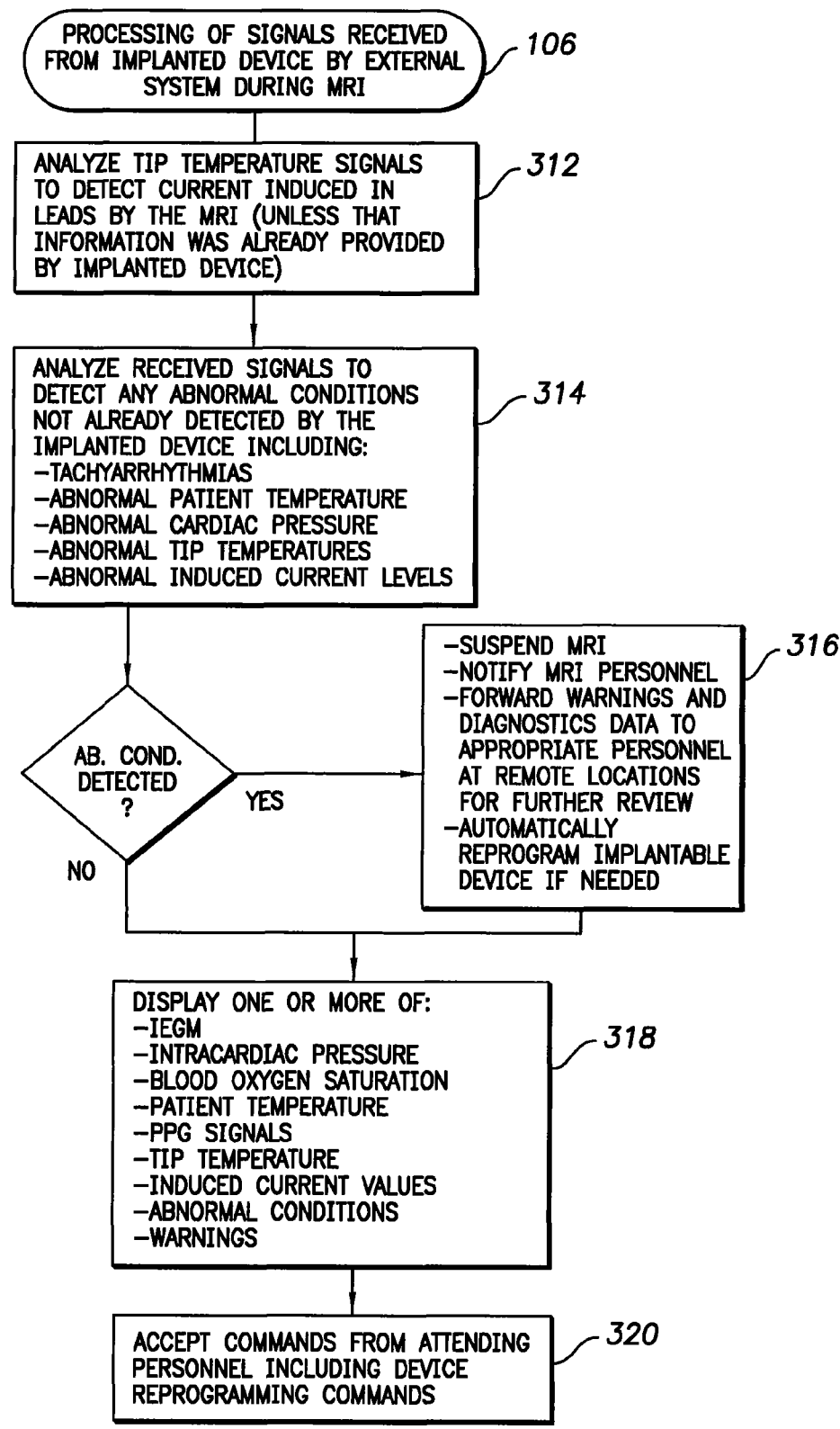
FIG. 7 is a flow diagram providing a more detailed illustration of exemplary processing techniques performed in accordance with the general techniques of FIG. 2, particularly signal analysis and display procedures performed by the external monitoring system during the MRI procedure.

Turning now to FIGS. 6-7, operations performed by the external monitoring system or other external or remote system will now be described in detail. In particular, FIG. 6 illustrates exemplary techniques that may be performed in accordance with step 104 of FIG. 3. Beginning at step 300, the external monitoring system detects the presence of the pacer/ICD based on signals received from the pacer/ICD in response to the aforementioned MRI proximity notification signals periodically transmitted by the external system. If no pacer/ICD is detected within the MRI procedure room, the external system continues to periodically transmit the notification signals, at step 302. Assuming, though, that a pacer/ICD responds to the notification signals, the external system then activates its long-range RF telemetry mode, at step 304, to beginning receiving data from the pacer/ICD. In implementations wherein the external system is not equipped to transmit the notification signals or the pacer/ICD is not equipped to respond to the signals, the long-range telemetry mode may be activated manually via appropriate input commands provided by the attending personnel. Alternatively, the long-range telemetry mode may remain active at all times to detect and respond to RF telemetry signals. The latter configuration may be particularly appropriate if the external system is a dedicated monitoring system provided exclusively for use in communicating with pacer/ICDs during MRI procedures. If, however, the external system is a portable programmer device that is also equipped to provide a wide range of pacer/ICD programming operations, then its long range MRI telemetry mode is preferably activated only when needed, i.e. only when the external programmer and a pacer/ICD are both in proximity to an MRI machine. In any case, as discussed above, the long range telemetry mode may exploit MICS band frequencies (402 MHz-405 MHz) or ISM band frequencies (2.5 GHz-5.0 GHz), and any communications protocols associated therewith. Whereas a particular pacer/ICD might be equipped to utilize only one of those two telemetry modes, the external system is preferably equipped to receive and transmit in either mode, so as to communicate with pacer/ICDs of either type. As already explained, the use of these communication channels helps ensure that data can be reliably transmitted from the pacer/ICD to the external system. Notch filters and/or adaptive slew rate filters of the type described above may also be provided within the telemetry components of the external system to filter out MRI fields and thereby provide for improved communication.

At step 306, the external system then begins receiving data transmitted from implantable device including the aforementioned electrophysiological signals and hemodynamic signals (e.g. IEGMs, intracardiac pressure values, blood oxygen saturation values, patient temperature values, PPG signals, etc.), as well as tip temperature values and induced current values, if provided by the pacer/ICD. As already noted, such signals can be received even before the MRI procedure begins. Such initial signals are preferably stored and displayed as "baseline" signals for comparison against subsequent signals received from the pacer/ICD during the actual MRI procedure. At step 308, the external system also receives warnings pertaining to abnormal conditions, if any, detected within the patient by the pacer/ICD. If any such warnings are received then, at step 310, the external system preferably forwards appropriate command signals to the MRI controller for suspending the MRI procedure. Suitable warning signals are also presented to immediately notify the attending MRI personnel, such as audible or visual alarms. Also, if appropriate, the warning signals and corresponding diagnostics data are forwarded to cardiologists or electrophysiologists at remote locations via the Internet or other communications network for further review. Typically, any such transmission of data to remote locations is performed only under the control of the medical personnel in the MRI procedure room in response to any conditions that the medical personal cannot diagnose or are unable to address. It should be understood that the forwarding of data for remote review is not performed in lieu of removing a patient from the MRI in response to a tachyarrhythmia. Rather, any serious arrhythmia is addressed immediately by the MRI personnel. Nevertheless, circumstances may arise where it is desirable to have IEGMs or other diagnostic data reviewed by experts at a remote location, time permitting.

FIG. 7 illustrates exemplary techniques that may be performed by the external monitoring system in accordance with step 106 of FIG. 3. At step 312, the external system analyzes tip temperature signals to estimate electrical currents induced in leads by the MRI, unless that information was already provided by implanted device. That is, in implementations where the pacer/ICD is equipped to provide tip temperature values but is not provided with the necessary software for estimating induce currents therefrom, the external system may perform that estimate (assuming it is provided with the necessary software, conversion values, etc.) Even in implementations where the pacer/ICD is equipped to provide induced current estimates, the external system may be equipped to provide more precise estimates using, e.g., more sophisticated analysis techniques than might be accommodated within the pacer/ICD.

At step 314, the pacer/ICD analyzes received signals to detect any abnormal conditions within the patient not already detected by the pacer/ICD including: tachyarrhythmias, abnormal patient temperatures, abnormal cardiac pressures, abnormal tip temperatures, and/or abnormal induced current levels. In this regard, more sophisticated analysis techniques may be performed by the external system than might be accommodated within the pacer/ICD. As one example, a pacer/ICD typically detects and distinguishes ventricular tachyarrhythmias merely be comparing the ventricular rate against one or more thresholds, as discussed above. The external system, in contrast, may perform a more sophisticated analysis of the morphology of the IEGM to detect and distinguish various arrhythmias. See, for example, U.S. Pat. No. 5,404,880 to Throne, entitled "Scatter Diagram Analysis System and Method for Discriminating Ventricular Tachyarrhythmias." Also, at step 314, newly received data signals can be compared against any previously received baseline signals, to facilitate the detection of abnormal conditions triggered by the MRI procedure.

At step 316, the pacer/ICD then takes the following actions (if not already performed at step 310 of FIG. 6): suspend the MRI, notify MRI personnel, forward warnings and diagnostics data to appropriate personnel at remote locations for further review. Also, at step 316, the external system may automatically reprogram the pacer/ICD, if needed, by sending appropriate programming signals to the pacer/ICD via long-range telemetry. In this regard, if the external system detects an arrhythmia that the pacer/ICD had failed to detect, the external programmer may reprogram the pacer/ICD accordingly so as to, e.g., switch the pacer/ICD from a tracking mode to a non-tracking mode.

At step 318, the external system displays one or more of: the patient's IEGM, intracardiac pressure, blood oxygen saturation, patient temperature, PPG signals, tip temperature values, induced current values, abnormal conditions, and any warnings, whether initially generated by the pacer/ICD or subsequently generated by the external system. Attending personal can then review the data and take action, at step 322, when appropriate. In this regard, the attending personnel might identity abnormal conditions that neither the pacer/ICD nor the external system automatically detected. The attending personnel may then forward the data to the remote location for expert review or may take whatever other steps are appropriate, such as manually suspending the MRI procedure (by entering appropriate commands into the input console of the MRI controller) or manually reprogramming the pacer/ICD (by entering appropriate re-programming commands into the input console of an external programmer for relaying to the pacer/ICD), etc. That is, at step 320, the external monitoring system accepts commands from attending personnel, including device reprogramming commands, in response to the displayed data and warning signals. In some implementations, the attending personnel may specify additional diagnostics data to be generated and forwarded by the pacer/ICD. For example, if the pacer/ICD is programmed to initially provide only IEGM data, the attending personal may reprogram the pacer/ICD during the MRI procedure to begin detecting and sending additional diagnostic information (blood pressure, $SO_2$, etc.) that might be of particular interest.

The techniques discussed above can be implemented in a wide variety of implantable medical device for use with a wide variety of external systems. For the sake of completeness, detailed descriptions of an exemplary pacer/ICD and an exemplary external monitoring system will now be provided.

Exemplary Pacer/ICD

Figure 8:
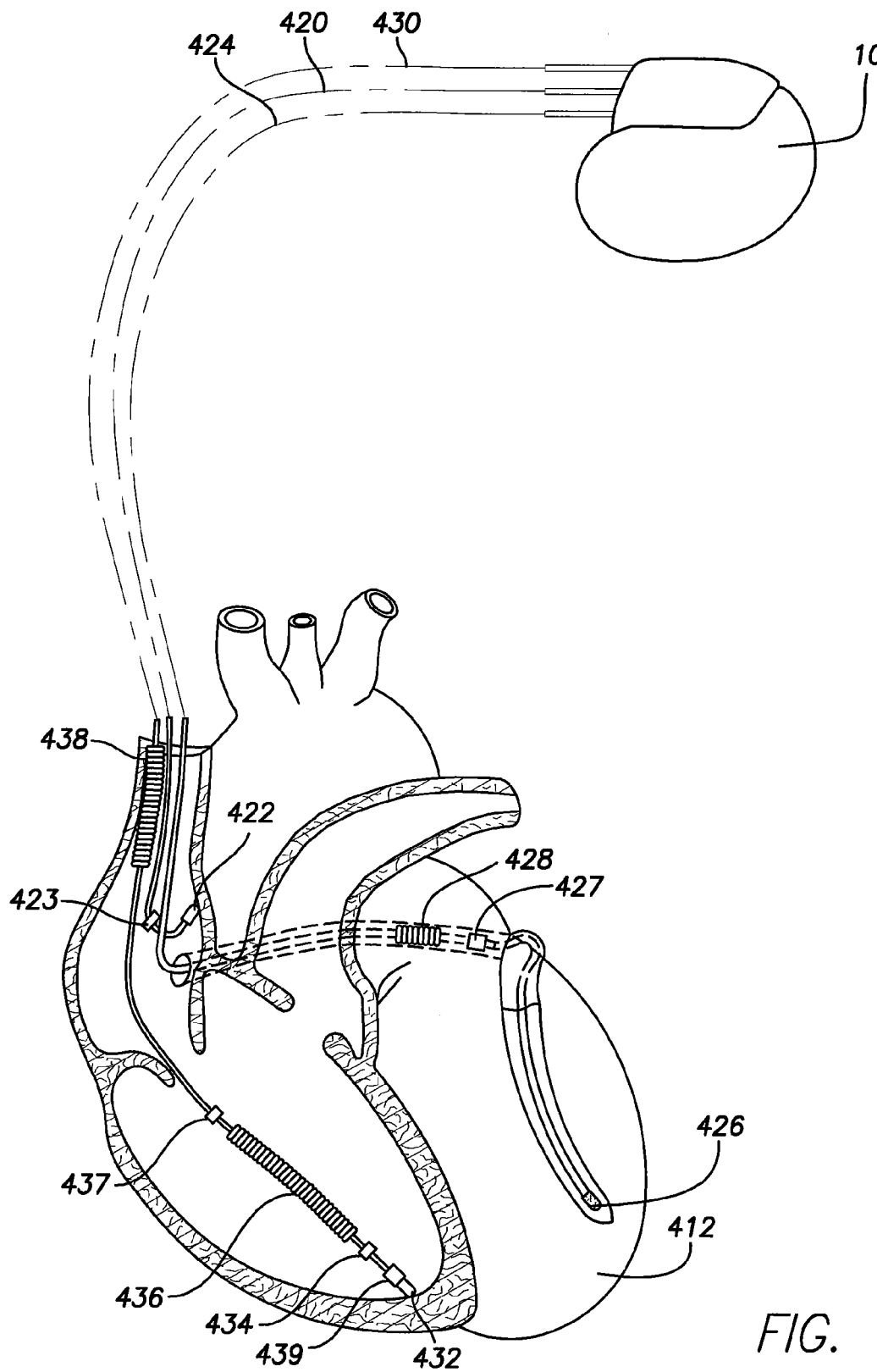
FIG. 8 is a simplified, partly cutaway view, illustrating the pacer/ICD of FIG. 1 along with a full set of leads implanted in the heart of the patient.

With reference to FIGS. 8 and 9, a description of the pacer/ICD of FIG. 1 will now be provided. FIG. 8 provides a simplified diagram of the pacer/ICD, which is a dual-chamber stimulation device capable of treating both fast and slow arrhythmias with stimulation therapy, including cardioversion, defibrillation, and pacing stimulation, as well as capable of detecting and responding to MRI fields.

To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424. The coronary sinus lead is designed for placement in the "coronary sinus region" via the coronary sinus os and is configured to position a distal electrode adjacent to the left ventricle and/or additional electrode (s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Additionally, a hemodynamic sensor 437 is shown mounted to the RV lead 430 that transmits one or more hemodynamic signals, such as RVP signals, to the pacer/ICD. Numerous other sensors can be mounted to the various pacing/sensing leads or to other leads. Also, a tip temperature sensor 439 is mounted near tip electrode 432 for sensing its temperature. Similar sensors may be mounted adjacent the tip electrodes of the other leads.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively. A sensor terminal 459 is provided for connection to hemodynamic sensor 437. A tip temperature electrode 461 is provided for connection to tip temperature sensor 439.

A set of adaptive slew rate filters and/or notch filters 463 are provided along the various terminals for filtering MRI-induced noise from input/output signals. As described above, depending upon the implementation, some or all of these filters may be selectively activated only in response to the presence of MRI signals. A magnetometer 465 may be provided for detecting MRI fields. An MRI-responsive sensing controller 501, discussed below, controls the activation of the filters in response to MRI fields detected by the magnetometer.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Switch 474 is configured to allow any output of the device to be selectively tri-stated, i.e. the switch includes internal components that allow outputs to be generated as normal bi-state outputs (positive vs. negative) or tri-sate outputs (positive, negative, open circuit.) This will be described in more detail below with reference to FIG. 6.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with an external device 502, such as a programmer, transtelephonic transceiver or a diagnostic system analyzer, or the external monitoring system 8 (FIG. 1). The telemetry circuit 500 is activated by the microcontroller by a control signal 506. The telemetry circuit 500 advantageously allows IEGMs and other electrophysiological signals and/or hemodynamic signals, tip temperature information, induce current information and status information relating to the operation of pacer/ICD 10 (as stored in the microcontroller 460 or memory 494) to be sent to the external programmer device 502 through an established communication link 504 or to a separate external monitoring system via link 509. To facilitate communication with the external monitoring system, MICs band and/or ISM band components 467 and 469 are provided within the telemetry circuit. Notch filters and/or adaptive slew rate filters may be provided within the telemetry circuit, as well.

Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient, such as sensor 437 of FIG. 8. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 9. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 512 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as MRI-responsive operations are concerned, the microcontroller includes an MRI-responsive signal detection controller 501, which is operative to control the detection of signals within the patient during an MRI procedure, wherein the detected signals include, at least, electrophysiological signals and/or hemodynamic signals, generally in accordance with the techniques described above in connection with FIG. 3. The microcontroller includes an MRI-responsive transmission controller 503, which is operative to control transmission of the detected signals to the external monitoring system during the MRI procedure, generally in accordance with the techniques described above in connection with FIG. 5. Moreover, the microcontroller includes a tip temperature-based induced current detector 505, which is operative to estimate induced current based on tip temperature values received via tip temperature terminal 461, generally in accordance with the techniques described above in connection with FIG. 3. Still further, the microcontroller includes a MRI response abnormal condition detector 507, which is operative to detect one or more abnormal conditions within the patient, such as abnormal temperatures, pressures, etc., also generally in accordance with the techniques described above.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary External Monitoring System

Figure 10:
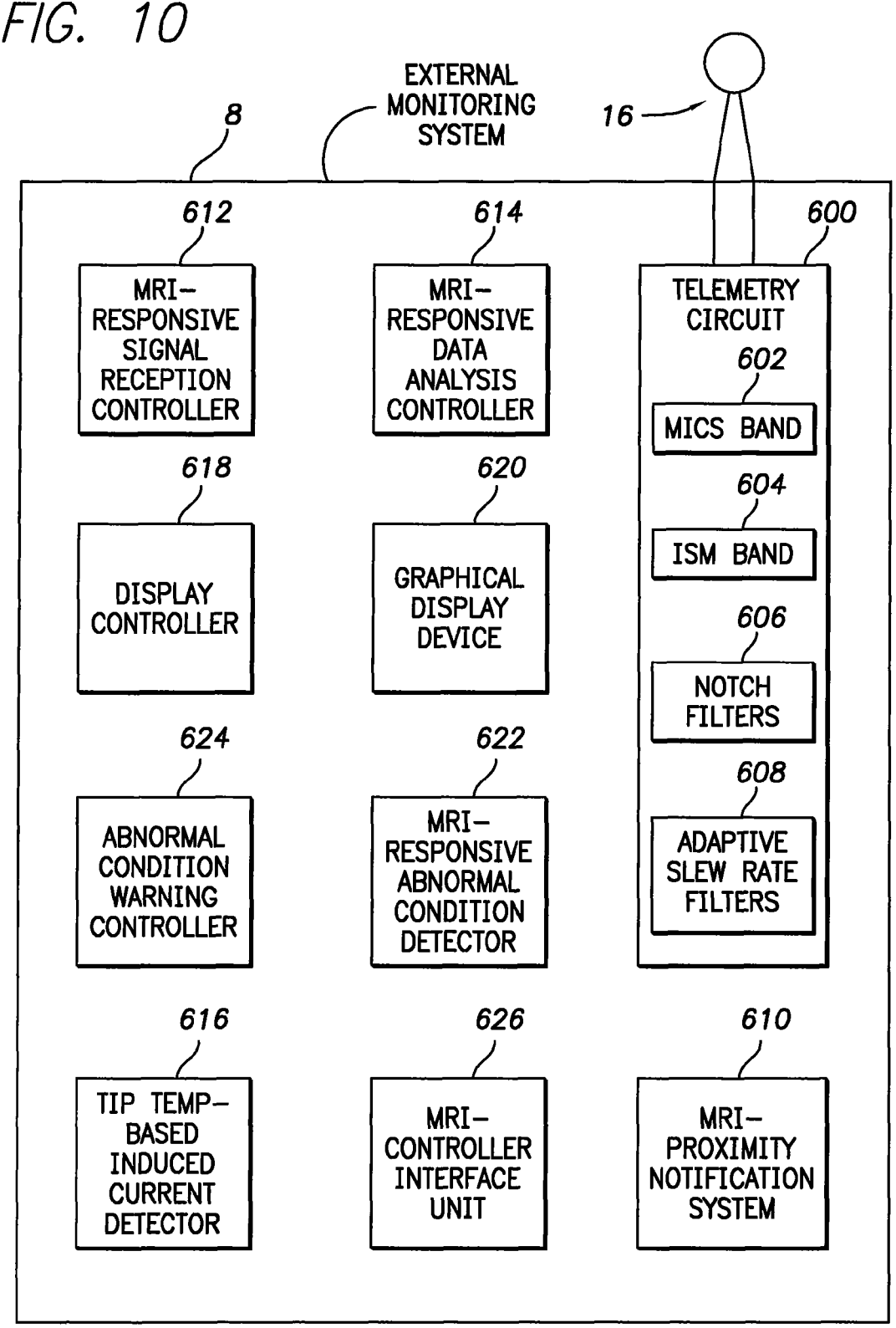
FIG. 10 is a functional block diagram illustrating components of an external monitoring system for use in receiving, analyzing and displaying signals received from the pacer/ICD of FIG. 9 during an MRI procedure.

With reference to FIG. 10, a brief description of an exemplary remote monitoring system 8 for use in the system of FIG. 1 will now be provided. Remote monitoring system 8 includes a telemetry circuit 600 connected to long range RF antenna 16 for communicating with a pacer/ICD or other implantable medical device. The telemetry circuit includes MICS band and ISM band components, 602 and 604, for controlling communication with the pacer/ICD in accordance with those protocols and at the frequencies specified for use therewith. Notch filters 606 and adaptive slew rate filters 608, shown in block diagram form, may be provided to filter noise from signals received from the pacer/ICD arising due to the MRI fields. An MRI proximity notification system 610 generates the periodic MRI proximity notification signals, discussed above, for notifying the pacer/ICD of its proximity to the MRI and for activating the MRI mode therein so that the pacer/ICD can then begin to transmit electrophysiological signals, hemodynamic signals and/or other signals to the external monitoring system. An MRI-responsive signal reception controller 612 controls the reception of signals from the pacer/ICD during the MRI procedure, generally in accordance with the techniques described above in connection with FIG. 6. An MRI-responsive data analysis controller 614 controls the analysis of signals received from the pacer/ICD during the MRI procedure, generally in accordance with the techniques described above in connection with FIG. 7. A tip temperature-based induced current detector 616 may be provided to estimate induced current levels within the leads of the patient based on tip temperature values received from the pacer/ICD, if that information is not already provided.

A display controller 618 controllers the generation of graphical displays of data received from the pacer/ICD and any data generated within the external system for display on a graphical display device 620, such as an LCD, CRT display or the like, also generally in accordance with techniques described above in connection with FIG. 7. An MRI-responsive abnormal condition controller 622 further analyses the diagnostic data to detect arrhythmias, abnormal temperature, pressures, etc. within the patient, also generally in accordance with techniques described above in connection with FIG. 7. Warnings pertaining to any abnormal conditions, either detected by the pacer/ICD or by the external system or both, are generated by abnormal condition warning controller 624 for display via display device 620 or via an audible warning device, also generally in accordance with techniques described above in connection with FIG. 7. An MRI controller interface unit 626 is provided for interfacing with the controller (block 6 of FIG. 1) of the MRI machine for sending signals to the MRI controller to suspend the MRI procedure, if warranted due to the detection of a tachyarrhythmia or other abnormal condition within the patient, also generally in accordance with techniques described above.

What have been described are various systems and methods for MRI-responsive operations using a pacer/ICD in conjunction with an external monitoring system. Principles of the invention may be exploiting using other implantable systems, externals systems or in accordance with other techniques. Thus, while the invention has been described with reference to particular exemplary embodiments, modifications can be made thereto without departing from the scope of the invention.

What is claimed is:

1. A method for use by an implantable medical device for implant within a patient, the method comprising:
    sensing signals within the patient during a magnetic imaging procedure;
    filtering the sensed signals to reduce the influence of MRI fields on the sensed signals;
    sensing a temperature during the MRI procedure that is associated with an electrode of a lead connected to the implantable medical device; and
    transmitting the filtered signals and the signals representative of the electrode temperature to an external monitoring system during the magnetic imaging procedure so that the signals can be remotely monitored during the magnetic imaging procedure.

2. The method of claim 1 wherein the magnetic imaging procedure is a magnetic resonance imaging (MRI) procedure.

3. The method of claim 2 wherein filtering the sensed signals to reduce the influence of MRI fields on the signals includes filtering the signals at frequencies associated with MRI fields.

4. The method of claim 3 wherein filtering the sensed signals to reduce the influence of MRI fields on the signals includes filtering the signals at slew rates associated with the MRI fields.

5. The method of claim 2 wherein transmitting the sensed signals to an external monitoring system during the MRI procedure includes transmitting the signals at frequencies associated with medical implant communication services (MICS) band frequencies.

6. The method of claim 2 wherein transmitting the sensed signals to an external monitoring system during the MRI procedure includes transmitting the signals at frequencies associated with industrial scientific medical (ISM) band frequencies.

7. The method of claim 2 further including the initial steps of:

sensing entry of the patient into an MRI procedure room; and in response thereto, activating an operational mode within the implanted device, wherein the sensing of signals within the patient during the MRI procedure and the transmission of the sensed signals to the external monitoring system during the MRI procedure are enabled.

8. A method for use by an implantable medical device for implant within a patient, the method comprising:

sensing signals within the patient during a magnetic imaging procedure;

filtering the sensed signals to reduce the influence of MRI fields on the sensed signals;

receiving a signal during the MRI procedure from a lead connected to the implanted device representative of changes during MRI scans in the temperature of an electrode of the lead; and transmitting the filtered signals and the signal representative of changes in the temperature of an electrode to an external monitoring system during the magnetic imaging procedure so that the signals can be remotely monitored during the magnetic imaging procedure.

9. A system for use with an implantable medical device for implant within a patient, the system for use during a magnetic resonance imaging (MRI) procedure, the system comprising:

an MRI-responsive signal sensing controller operative to control the sensing and filtering of signals during the MRI procedure, the signals filtered to reduce the interaction influence of MRI fields on the sensed signals;

a temperature sensor adapted to measure a temperature associated with an electrode of a lead connected to the implantable medical device during the MRI procedure; and an MRI-responsive data transmission controller operative to control transmission of the sensed signals to an external monitoring system during the MRI procedure, such that the signals can be remotely monitored during the MRI procedure.

\* \* \* \* \*